(12) United States Patent
Smoot et al.

(10) Patent No.: US 7,690,115 B2
(45) Date of Patent: *Apr. 6, 2010

(54) METHOD OF MAKING A MICRO-FLUID EJECTION DEVICE

(75) Inventors: Mary C. Smoot, Lexington, KY (US); Paul T. Spivey, Lexington, KY (US); Melissa M. Waldeck, Lexington, KY (US); Craig M. Bertelsen, Union, KY (US); Sean T. Weaver, Union, KY (US)

(73) Assignee: Lexmark International, Inc., Lexington, KY (US)

( * ) Notice: Subject to any disclaimer, the term of this patent is extended or adjusted under 35 U.S.C. 154(b) by 852 days.

This patent is subject to a terminal disclaimer.

(21) Appl. No.: 11/386,174

(22) Filed: Mar. 22, 2006

(65) Prior Publication Data

US 2006/0213060 A1   Sep. 28, 2006

Related U.S. Application Data

(63) Continuation of application No. 10/880,899, filed on Jun. 30, 2004, now Pat. No. 7,043,838.

(51) Int. Cl.
*B21D 53/76* (2006.01)
*B32B 38/14* (2006.01)

(52) U.S. Cl. .................. 29/890.1; 29/832; 156/277; 347/47

(58) Field of Classification Search ............... 29/890.1, 29/832; 438/21; 347/40, 47; 156/250, 256, 156/264, 277, 278
See application file for complete search history.

(56) References Cited

U.S. PATENT DOCUMENTS 4,734,717 A * 3/1988 Rayfield .............. 347/47 X
4,741,603 A * 5/1988 Miyagi et al. ............ 359/270

FOREIGN PATENT DOCUMENTS

JP          05042672 A  *  2/1993   ............ 29/890.1 X

* cited by examiner

*Primary Examiner*—A. Dexter Tugbang

(57) ABSTRACT

A method is provided for making a multi-fluid cartridge for holding multiple fluids in segregated containment localities. The cartridge body contains fluid supply paths in fluid flow communication with the containment localities. A nozzle plate is attached to a device side of each of a plurality of defined ejection head substrates on a semiconductor wafer. Each of the ejection head substrates has a fluid supply side and two or more fluid flow paths therein for supplying fluid from the supply side to the device side thereof. The fluid flow paths in the ejection head substrates have a flow path density of greater than about 1.0 flow paths per millimeter. The wafer is diced to provide a plurality of micro-fluid ejection device structures. A circuit device is attached to the device side of each of the substrates. An adhesive is stencil printed with a bond line density of at least about $1.2\,\text{mm}^{-1}$ on the micro-fluid ejection device structures or on the cartridge body. At least one of the micro-fluid ejection device structures and attached circuit is adhesively bonded to the cartridge body for flow of fluid from the containment localities to the device side thereof.

13 Claims, 10 Drawing Sheets

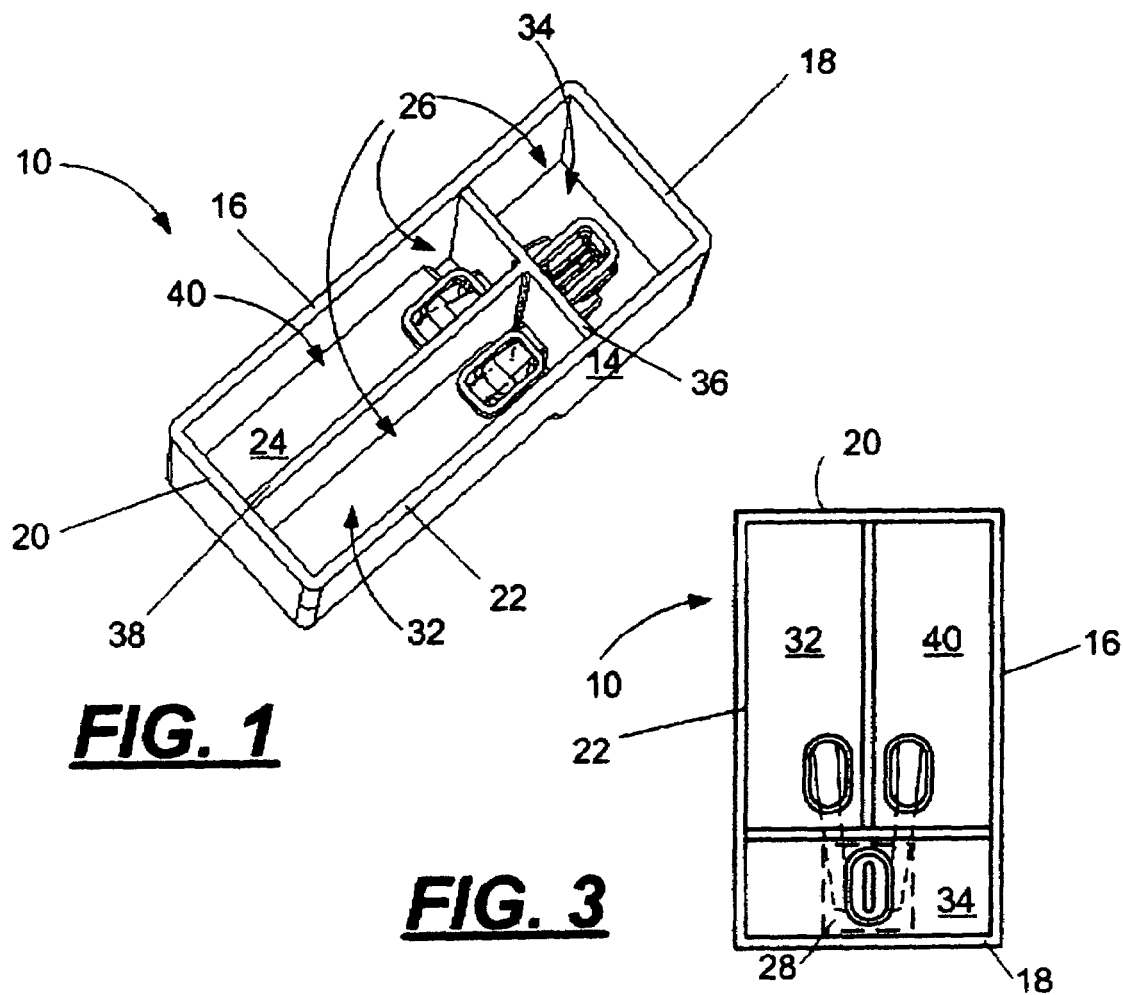
FIG. 1
FIG. 3
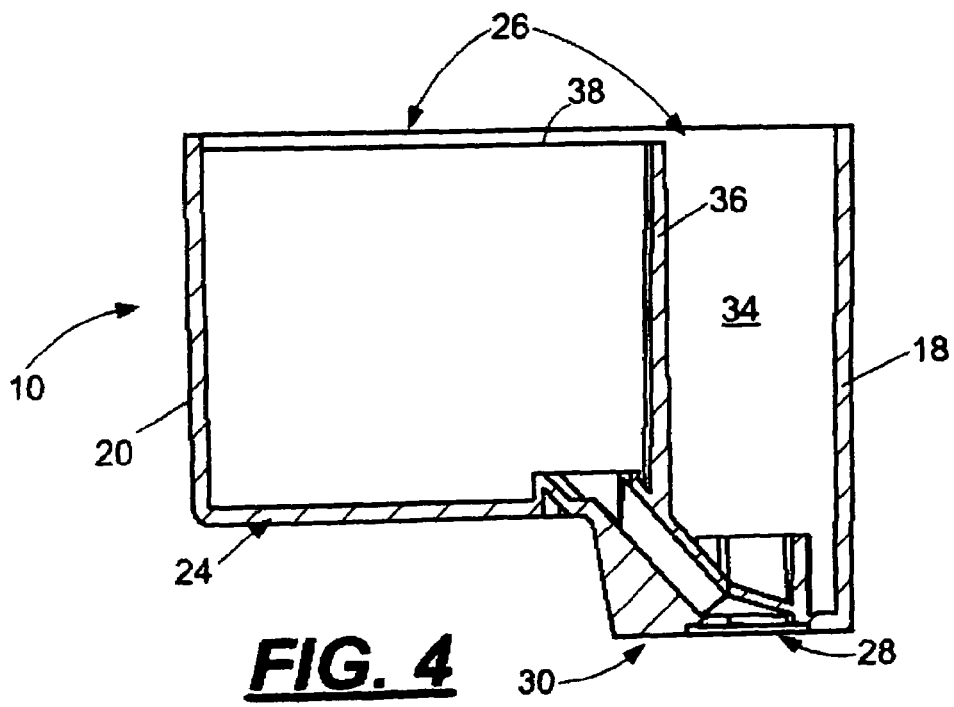
FIG. 4

METHOD OF MAKING A MICRO-FLUID EJECTION DEVICE

This application is a continuation of prior application Ser. No. 10/880,899, filed on Jun. 30, 2004 now U.S. Pat. No. 7,043,838, the entire disclosure of which is hereby incorporated by reference.

FIELD OF THE INVENTION

The disclosure relates to micro-fluid ejection devices and in particular to structures and techniques for securing a semiconductor substrate to a multi-fluid reservoir.

BACKGROUND OF THE INVENTION

In the field of micro-fluid ejection devices, ink jet printers are an exemplary application where miniaturization continues to be pursued. However, as micro-fluid ejection devices get smaller, there is an increasing need for unique designs and improved production techniques to achieve the miniaturization goals. For example, the increasing demand of putting more colors in a single inkjet cartridge requires the addition of fluid flow passageways from the cartridge body to the ejection head that, without radical changes in production techniques, will require larger ejection head substrates. However, the trend is to further miniaturize the ejection devices and thus provide smaller ejection head substrates. An advantage of smaller ejection head substrates is a reduction in material cost for the ejection heads. However, this trend leads to challenges relating to attaching such substrates to a multi-fluid supply reservoir.

As the ejection heads are reduced in size, it becomes increasingly difficult to adequately segregate multiple fluids in the cartridges from one another yet provide the fluids to different areas of the ejection heads. One of the limits on spacing of fluid passageways in the ejection head substrate is an ability to provide correspondingly small, and closely-spaced passageways from the fluid reservoir to the ejection head substrate. Another limit on fluid passageway spacing is the ability to adequately align the passageways in the fluid reservoir with the passageways in the ejection head substrate so that the passageways are not partially or fully blocked by an adhesive used to attach to the ejection head to the reservoir.

Thus, there continues to be a need for improved structures and manufacturing techniques for micro-fluid ejection head components for ejecting multiple fluids onto a medium.

SUMMARY OF THE INVENTION

With regard to the foregoing, the disclosure provides a micro-fluid ejection device structure, a multi-fluid cartridge containing the ejection device structure, and methods for making the ejection device structure and cartridge. In one embodiment, a method is provided for making a multi-fluid cartridge for holding multiple fluids in segregated containment localities. The cartridge body contains fluid supply paths in fluid flow communication with the containment localities. A nozzle plate is attached to a device side of each of a plurality of defined ejection head substrates on a semiconductor wafer. Each of the ejection head substrates has a fluid supply side and two or more fluid flow paths therein for supplying fluid from the supply side to the device side thereof. The fluid flow paths in the ejection head substrates have a flow path density of greater than about 1.0 flow paths per millimeter. The wafer is diced to provide a plurality of micro-fluid ejection device structures. A circuit device is attached to the device side of each of the substrates. An adhesive is stencil printed with a bond line density of at least about 1.2 mm$^{-1}$ on the micro-fluid ejection device structures or on the cartridge body. At least one of the micro-fluid ejection device structures and attached circuit is adhesively bonded to the cartridge body for flow of fluid from the containment localities to the device side thereof.

One advantage of the apparatus and methods disclosed herein could be that multiple different fluids can be ejected from a micro-fluid ejection device that is less costly to manufacture and has dimensions that enable increased miniaturization of operative parts of the device. Continued miniaturization of the operative parts enables micro-fluid ejection devices to be used in a wider variety of applications. Such miniaturization also enables the production of ejection devices, such as printers, having smaller footprints without sacrificing print quality or print speed. The apparatus and methods described might reduce the size of a silicon substrate used in such micro-fluid ejection devices without sacrificing the ability to suitably eject multiple different fluids from the ejection device.

BRIEF DESCRIPTION OF THE DRAWINGS

Further advantages of the embodiments described herein will become apparent by reference to the detailed description of exemplary embodiments when considered in conjunction with the drawings, wherein like reference characters designate like or similar elements throughout the several drawings as follows:

FIG. 1 is a top perspective view of an inside cavity of a multi-fluid cartridge body according to the disclosure;

FIG. 3 is a top plan view of a multi-fluid cartridge body according to the disclosure;

FIG. 4 is a side cross-sectional view of a multi-fluid cartridge body according to the disclosure;

DETAILED DESCRIPTION

Figure 2:
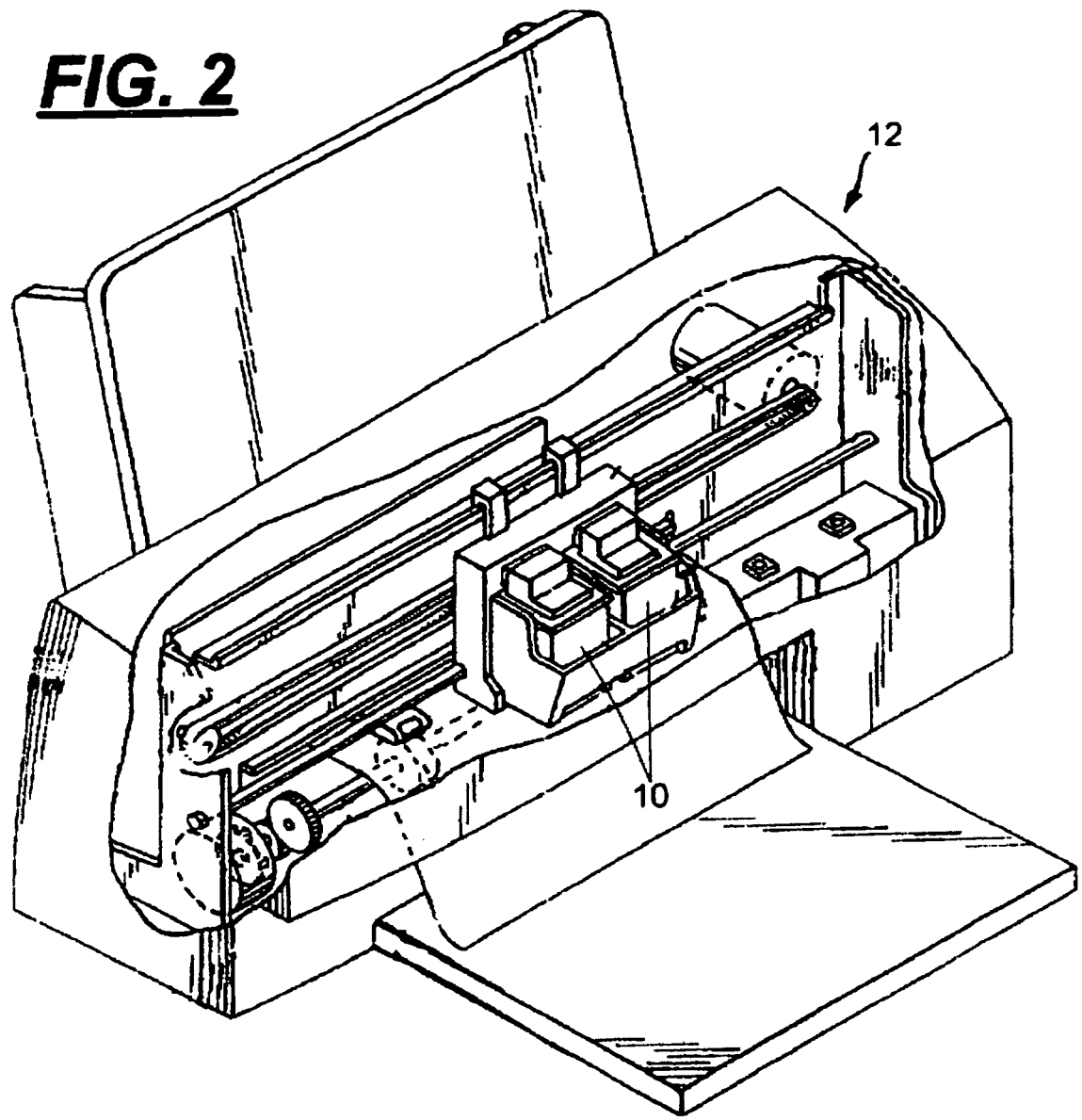
FIG. 2 is a perspective view of a micro-fluid ejection device.
Figure 5:
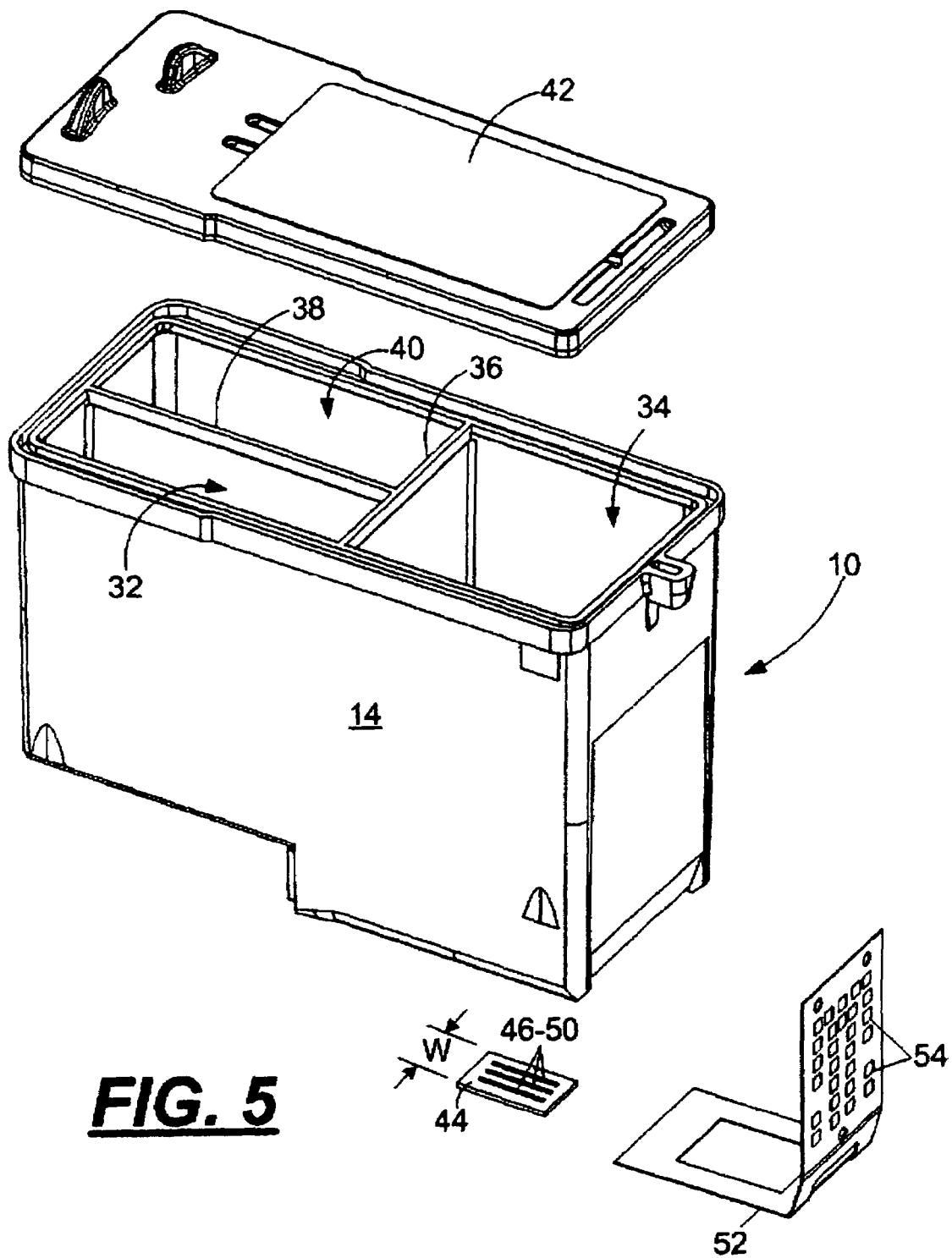
FIG. 5 is a perspective exploded view of a multi-fluid cartridge body according to the disclosure.

With reference to FIGS. 1-5, a multi-fluid cartridge body 10 for a micro-fluid ejection device, such as an ink jet printer 12 is illustrated. The multi-fluid body 10 includes a body structure 14 having exterior side walls 16, 18, 20, and 22 and a bottom wall 24 forming an open-topped, interior cavity 26. An ejection head area 28 is disposed adjacent a portion 30 of the bottom wall 24 opposite the interior cavity 26. At least two segregated fluid chambers 32 and 34 are provided within the interior cavity 26 of the body 10. A dividing wall 36 separates chamber 32 from chamber 34. An additional dividing wall 38 may be provided to separate chamber 40 from chamber 32 for a body 10 containing three different fluids. Independent fluid supply paths are provided from each of the fluid chambers 32, 34, and 40 to provide fluid to an ejection head structure 44 attached adjacent the ejection head area 28 of the body 10. The fluids are retained in the chambers 32, 34, and 40 by a cover 42 attached to the fluid body 10.

The body structure 14 is preferably molded as a unitary piece in a thermoplastic molding process. A preferred material for the body structure 14 is a polymeric material selected from the group consisting of glass-filled polybutylene terephthalate available from G.E. Plastics of Huntersville, N.C. under the trade name VALOX 855, amorphous thermoplastic polyetherimide available from G.E. Plastics under the trade name ULTEM 1010, glass-filled thermoplastic polyethylene terephthalate resin available from E. I. du Pont de Nemours and Company of Wilmington, Del. under the trade name RYNITE, syndiotactic polystyrene containing glass fiber available from Dow Chemical Company of Midland, Mich. under the trade name QUESTRA, polyphenylene ether/polystyrene alloy resin available from G.E. Plastics under the trade names NORYL SEI and NORYL 300X and polyamide/poly-phenylene ether alloy resin available from G.E. Plastics under the trade name NORYL GTX. A preferred material for making the body structure 14 is NORYL SEI resin.

Ejection head structure 44 contains fluid ejection actuators such as heater resistors or piezoelectric devices to eject fluid from the ejection head structure 44. Fluid to the actuators is provided from the body 10 to corresponding fluid flow paths 46-50 in the ejection head structure 44. A flexible circuit 52 containing electrical contacts 54 thereon is provided and attached to the ejection head structure 44 and body 10 to provide electrical energy to the actuators when the body 10 is attached to an ejection device such as ink jet printer 12.

Providing two or more chambers 32, 34, and 40 in a single body 10 increases the technical difficulties of using an injection molding process for making the body 10. If the body 10 is to be molded from a polymeric material as a single molded unit, there are significant challenges to molding suitable fluid supply paths in the body 10 to the ejection head area 28 using conventional mold construction and molding techniques. Such challenges include, but are not limited to, the complexity of cooling and filling the mold used for the injection molding process.

Figure 6:
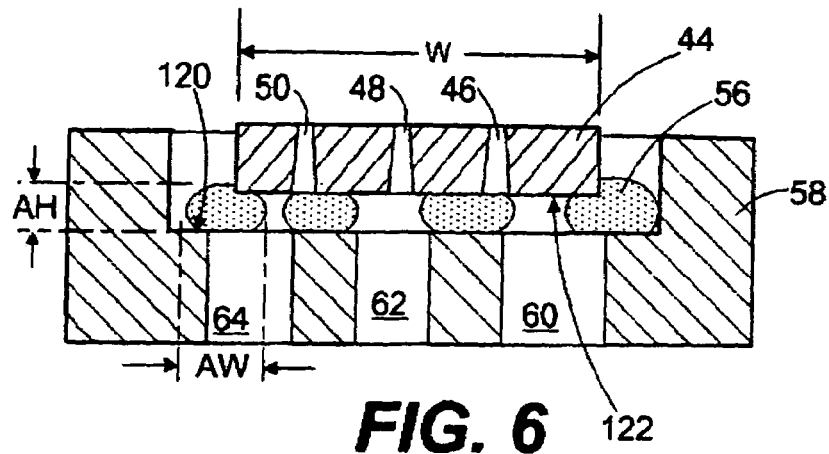
FIG. 6 is a cross-sectional view, not to scale of a micro-fluid ejection structure attached to a multi-fluid cartridge body.

A multi-fluid body, such as body 10, also presents challenges for sealing the ejection head structure 44 to the ejection head area 28 without blocking narrow fluid passageways in the ejection head area 28 of the body 10. For example, as shown in FIG. 6, an ejection head structure 44 having fluid flow paths 46, 48, and 50 therein is attached as by a die bond adhesive 56 to a multi-fluid body 58 having fluid supply paths 60, 62, and 64 therein. For a narrow ejection head structure 44 having a high density of fluid flow paths 46-50, it is difficult to adhere such head structure 44 directly to the body 58 using conventional adhesive techniques. In this case, fluid flow paths 46 and 50 are blocked or are partially blocked by the adhesive 56.

For purposes of this disclosure, the number of fluid supply paths within a given linear dimension W is defined as the flow path density. The term "high density" means that for a given dimension W of the ejection head structure 44, there are more than one fluid flow paths 46-50 per millimeter.

Figure 7:
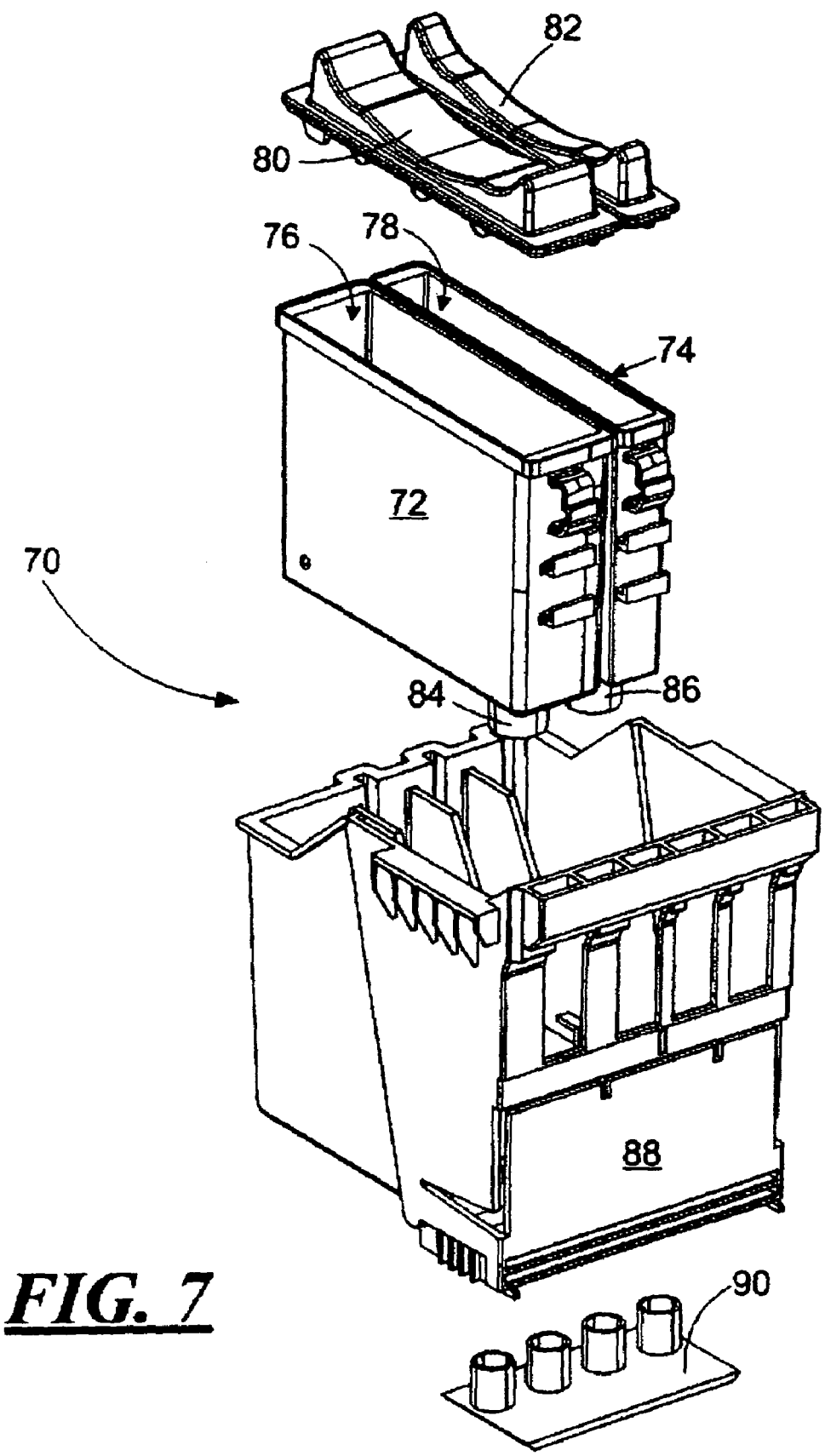
FIG. 7 is an exploded perspective view, not to scale, of a multi-fluid cartridge body made according to another embodiment of the disclosure.

Yet another multi-fluid body 70 is illustrated in FIG. 7. In FIG. 7, instead of a single multi-compartmentalized body 10 as illustrated in FIGS. 1 and 3-5, individual fluid containers such as fluid containers 72 and 74 are provided. The fluid containers 72 and 74 have fluid cavities 76 and 78 therein for different fluids. The fluid cavities 76 and 78 are closed by covers 80 and 82. A fluid outlet port 84, 86 is provided for each container 72, 74. The containers 72, 74 are inserted into a container housing 88 that contains a standpipe assembly 90 for fluidly coupling the outlet ports 84, 86 of the containers 72, 74 to an ejection head structure such as ejection head structure 44. The outlet ports 84, 86 of the containers 72, 74 are fluidly coupled to the standpipe assembly 90 when the containers 72, 74 are disposed in the container housing 88.

Figure 8:
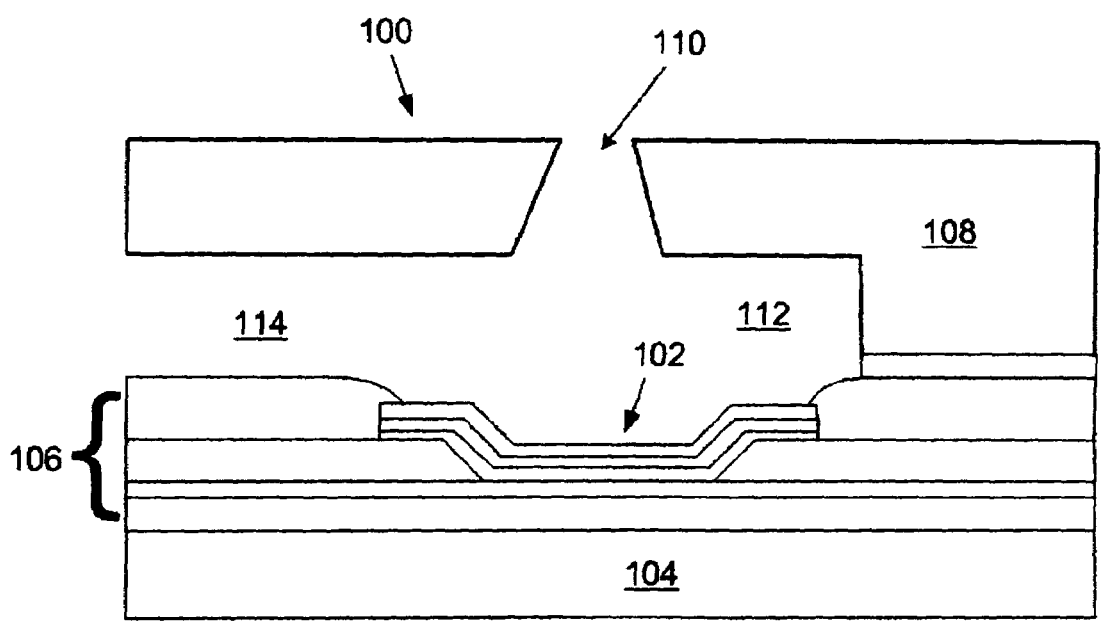
FIG. 8 is a cross-sectional view not to scale of a portion of a micro-fluid ejection head structure attached.

A portion 100 of a typical micro-fluid ejection device structure 44 is illustrated in FIG. 8. The portion 100 illustrated in FIG. 8 contains a thermal fluid ejection device 102. The portion 100 also includes a semiconductor substrate 104 containing multiple conductive, insulative, and protective layers 106 for forming and protecting the fluid ejection device 102. A nozzle plate 108 containing nozzle holes 110 is attached to the substrate 104 and layers 106 to provide a fluid ejection chamber 112. Fluid flows to the fluid ejection chamber 112 from the cartridge body 10, or containers 72, 74 through a fluid supply channel 114 that is in flow communication with the fluid flow paths 46-50 in the micro-fluid ejection device structure 44. While a thermal fluid ejection device 102 is illustrated in FIG. 8, the disclosure is also applicable to other types of fluid ejection devices including, but not limited to, piezoelectric fluid ejection devices.

It will be appreciated that as the number of fluid cavities for providing different fluids to the ejection device structure 44 increases, it becomes increasingly difficult to align and attach the ejection device structure 44 to the ejection head area 28 of the body 10. As described in more detail below, there are several unique solutions to the problem associated with increasing the number of fluid flow paths 46-50 per width W of the ejection device structure 44. The below described solutions also enable narrower, and thus smaller ejection device structures 44 to be used for multi-fluid bodies than would otherwise be suitable for such applications.

In one embodiment there is provided a method of dispensing an adhesive for bonding a micro-fluid ejection device structure to a multi-fluid body. Typically, the adhesive 56 is dispensed with a needle to a bonding area 120 of the body 58 (FIG. 6). Adhesive 56 dispensed in this manner has a bond line width AW of about 500 microns and a bond line height AH of about 100 microns. While the ejection head structure 44 typically has a substantially planar surface 122 for bonding to the body 58, the body 58 may not have such the substantially planar surface area 120 for bonding.

For suitably sealing between fluid flow paths 46-50, the planarity of the bonding surface 120 of the body 58 is preferably controlled within plus or minus 50 microns. However, for smaller bond line widths AW, smaller bond line heights AH are required. For a bond line width of 200 microns, the desired bond line height AH is about 25 microns. Accordingly, the planarity of the bonding surface 120 of the body 58 should be controlled within plus or minus 10 microns to get a good seal between flow paths 46-50 during a step used to bond the structure 44 to the body 58.

Figure 9:
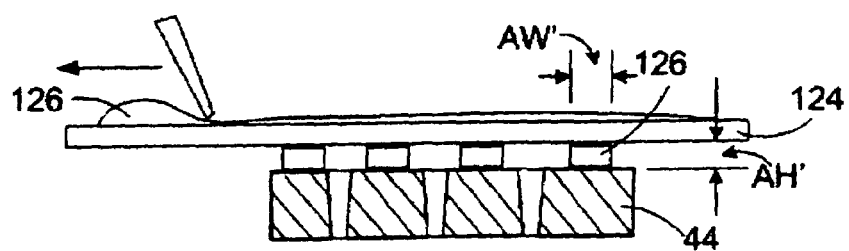
FIG. 9 is a schematic view of an adhesive application process for a micro-fluid ejection device structure according to the disclosure.

An improved method of bonding, according to one embodiment of the disclosure, includes a stencil or screen printing method for applying the adhesive to the ejection head structure 44 or body 10. According to the method, as illustrated schematically in FIG. 9, a stencil or screen 124 having precisely placed openings is used to apply an adhesive 126 on the ejection head structure 44 or on the body 10 in the ejection head area 28. Such a process will enable bond line widths AW down to about 10 microns and bond line heights AH down to or below about 10 microns. A preferred bond line width AW' ranges from about 10 to about 500 microns, preferably from about 200 to about 400 microns. Such bond line dimensions for the adhesive 126 enable an ejection head structure width W reduction directly proportional to a total area required for the adhesive bond lines.

Another advantage of stencil and/or screen printing the adhesive 126 on the ejection head structure 44 could be that over compression of the adhesive 126 in the bonding area between the head structure 44 and the body 10 is minimized. Adhesive over compression can lead to adhesive bulging into the fluid flow paths 50 and 46 as illustrated in FIG. 6. Accordingly, an adhesive applied to the ejection head structure 44 or body 58 using a conventional needle dispensing technique and having an adhesive bond line width AW of 550 microns may be over compressed during bonding resulting in an adhesive bulge with an overall width of 650 microns. Such a bulge in the adhesive 56 may cause flow restriction or blockage as shown in FIG. 6. The more precise stencil and screen printing method of applying the adhesive 126 provides improved control over adhesive bond line height AH' and thus over adhesive over compression during bonding.

Tighter control over the bond line height and bond line width enables a greater density of adhesive bond lines to be applied to the head structure 44 or body 10. A greater density of adhesive bond lines can provide either more bond lines for a given bonding area or can provide the ability to bond a smaller ejection head structure 44 to the body 10. In this case, the bond line width AW' is equivalent to the amount of adhesive required to seal between adjacent flow paths 46-50.

Figure 10:
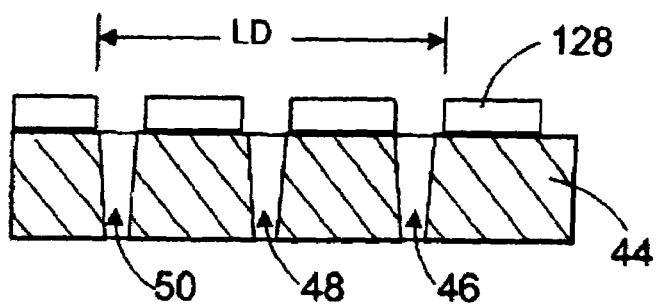
FIG. 10 is a cross-sectional view, not to scale, of a stencil or screen printed adhesive on a micro-fluid ejection device structure according to the disclosure.

For an ejection head structure 44 having 3 parallel flow paths 46-50, four bond lines 128 (FIG. 10) seal the ejection head structure 44 to the body 10. An ejection head structure containing n number of parallel flow paths 46-50 will typically utilize n+1 of the bond lines 128 to seal the flow paths to the body 10. An exception to this is when a fluid chamber in a body provides the same fluid to two or more of the flow paths in the ejection head structure. Accordingly, the foregoing method enables a substantial increase in bond line density. For the purposes of this disclosure, the bond line density is defined as the number of the bond lines 128 between parallel flow paths 46-50 divided by a linear distance LD between the flow paths 46-50 as shown in FIG. 10. Conventional technology enables a bond line density of about 0.7 $mm^{-1}$. The foregoing stencil and/or screen printing method enables bond line densities of greater than about 0.7 $mm^{-1}$, preferably from about 0.8 to about 2 $mm^{-1}$.

Materials that may be used as die bond materials or adhesives 126 for such applications include, but are not limited to, 3193-17 from Emerson and Cumings, M308.1 from EMS and 504-48 from EMS. These materials are also chemically compatible with the body material (NORYL SEI) describe above. When the die bond area becomes smaller and smaller, precision alignment of the paths and/or channels is crucial.

Figure 11:
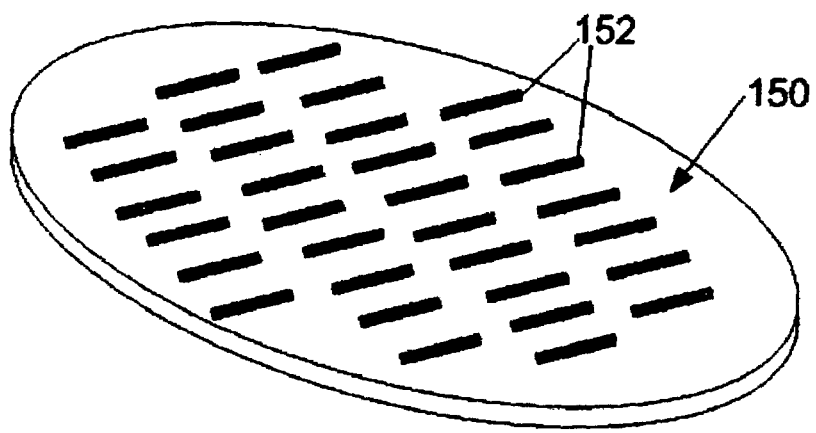
FIG. 11 is a perspective view not to scale of a semiconductor wafer with a plurality of ejection head substrates.
Figure 12:
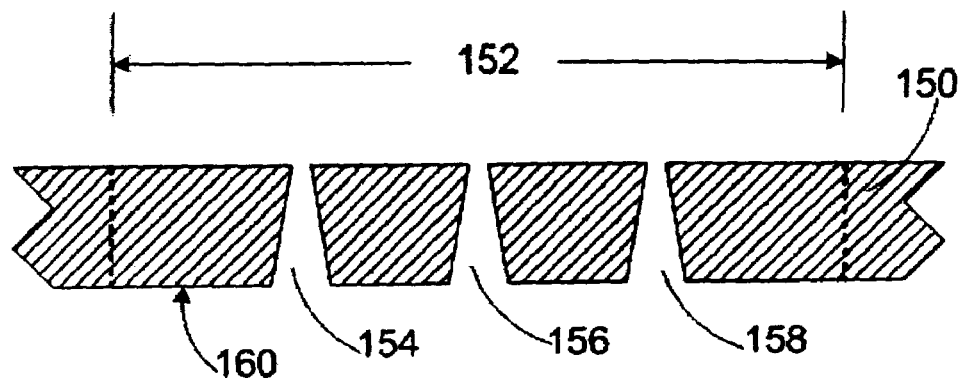
FIG. 12 is a cross-sectional view, not to scale of a portion of a semiconductor wafer with an ejection head substrate.
Figure 13:
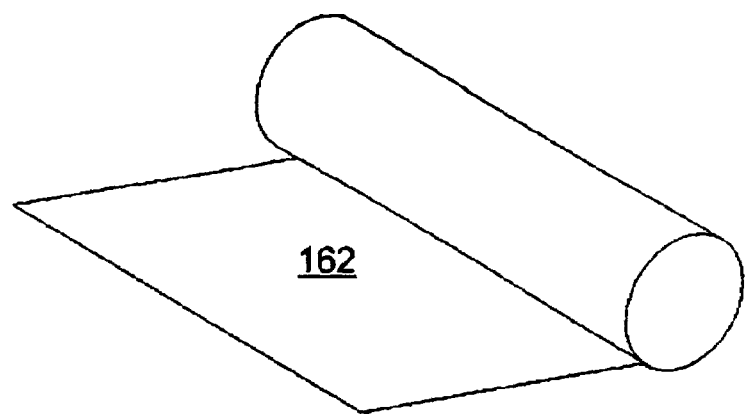
FIG. 13 is a perspective view, not to scale, of a photoresist laminate material for applying to a semiconductor wafer according to the disclosure.

An increase in flexibility of design for smaller ejection head structure 45 may also be provided by use of one or more of the following embodiments incorporating a photoresist manifold structure. According to one such embodiment, a photoresist material, either a positive or negative photoresist material, is applied to a semiconductor wafer 150 having a plurality of semiconductor substrates 152 defined thereon as shown in FIG. 11. Each of the substrates 152 contains ejection devices as described above on a device side thereof. The substrates 152 also contain flow paths formed therein, such as flow paths 154-158 (FIG. 12). According to the process, a photoresist material is applied to a fluid supply side 160 of the wafer 150. The photoresist material may be spin or spray-coated onto the wafer 150 or applied as a film or web 162 (FIG. 13) to the wafer 150.

Commercially available dry film photoresist materials include acrylic based materials, such as a material available from Mitsui of Japan under the trade name Ordyl PR132, epoxy based materials, such as a material available from E. I. DuPont de Nemours and Company Corporation of Wilmington, Del. under the trade name RISTON, or a material available from MicroChem Corporation of Newton, Mass. under the trade name SU-8 (or such as a proprietary material internally used at Lexmark International, Inc. of Lexington, Ky. and referred to internally as GSP920), and polyimide-based photoresist materials, such as a material available from HD Microsystems of Parlin, N.J. under the trade name HD4000.

Figure 14:
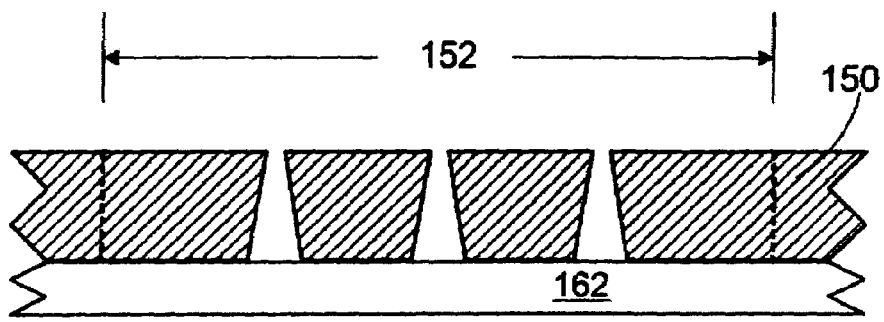
FIG. 14 is a cross-sectional view, not to scale, of a semiconductor wafer with a photoresist material layer.
Figure 15:
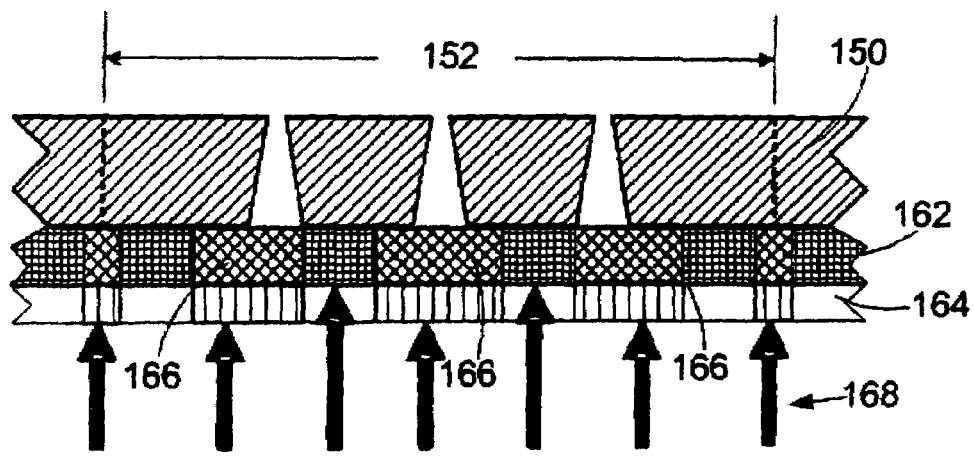
FIG. 15 is a schematic illustration of a patterning process for a photoresist material layer on a semiconductor wafer according to the disclosure.
Figure 16:
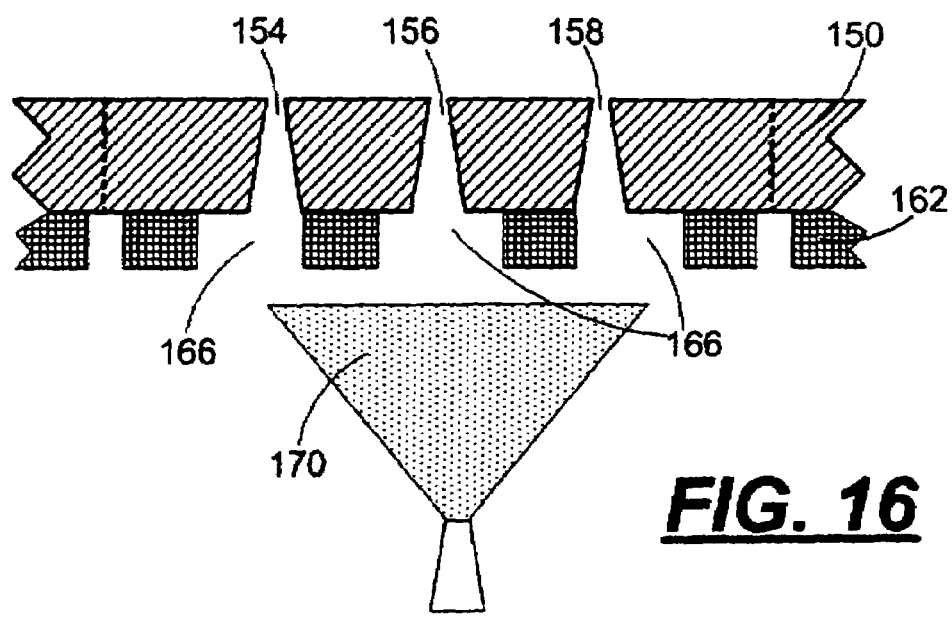
FIG. 16 is a schematic illustration of a developing process for a photoresist material layer on a semiconductor wafer according to the disclosure.

After applying the photoresist material 162 to the fluid supply side 160 of the wafer 150 (FIG. 14), the photoresist material 162 is exposed, as through a mask 164 to actinic radiation 168, such as ultraviolet (UV) light (FIG. 15) to pattern the photoresist material 162 to provide locations 166 for fluid flow channels in the photoresist material 162 upon developing the photoresist material 162. The patterned photoresist material 162 is then developed by dissolving uncured material from the fluid supply side 160 of the wafer 150 as shown in FIG. 16 using a developing chemical 170. The developing chemicals 170 may be selected from tetramethyl ammonium hydroxide, xylene or aliphatic hydrocarbons, sodium carbonate, and 2-butyl cellosolve acetate (BCA).

In an exemplary embodiment, the dry film photoresist material 162 is laminated to the wafer 150 at a temperature of about 50° C. and a pressure of 60 pounds per square inch gauge. The photoresist material 162 is exposed to UV radiation through the mask 164 for about four seconds at an energy of 18.6 milliwatts. After patterning the photoresist material, a development step is performed in which BCA is puddled onto the exposed photoresist material from about 1 minute. Next, BCA is sprayed onto the photoresist material for about 30 seconds. The wafer 150 is spin-dried for about 30 seconds. Then the photoresist material 162 is cured at about 180° C. for about two hours. The cured photoresist material 162 has the fluid flow channels 166 therein in fluid flow communication with the fluid flow paths 154-158 in the substrate 152.

Figure 17:
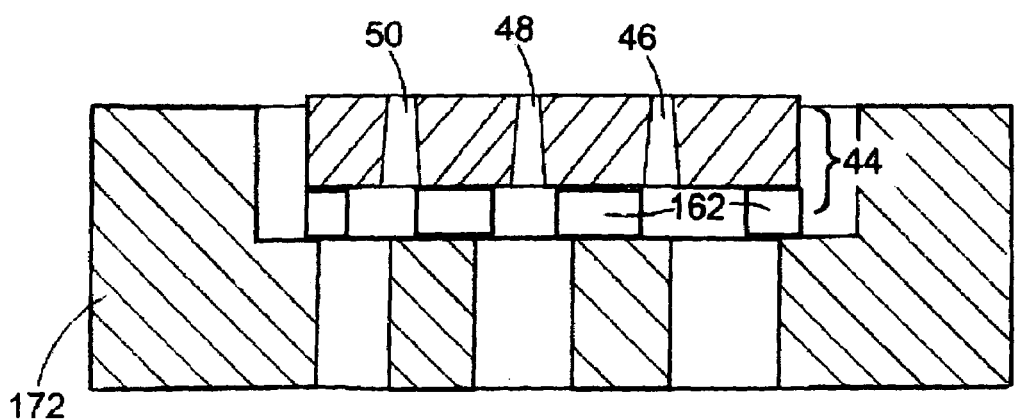
FIGS. 17-18 are cross-sectional views, not to scale, of ejection head structures attached to multi-fluid cartridge bodies according to embodiments of the disclosure.

After curing the photoresist material 162, a nozzle plate is attached to each of the substrates 152 to provide the ejection head structure 44 described above with reference to FIG. 6. The wafer 150 is then diced to provide individual ejection head structures 44 and flexible circuits, such as circuits 52, are electrically connected to the ejection head structures 44. Depending on the adhesive characteristics of the photoresist material 162, the ejection head structures 44 may be compression bonded to the body 10 or an adhesive may be applied to the photoresist material 162 on the ejection head structure or to the body 10 using the stencil or screen printing method described above. An illustration of an ejection head structure 44 attached to a body 172 as described above is illustrated in FIG. 17.

Figure 18:
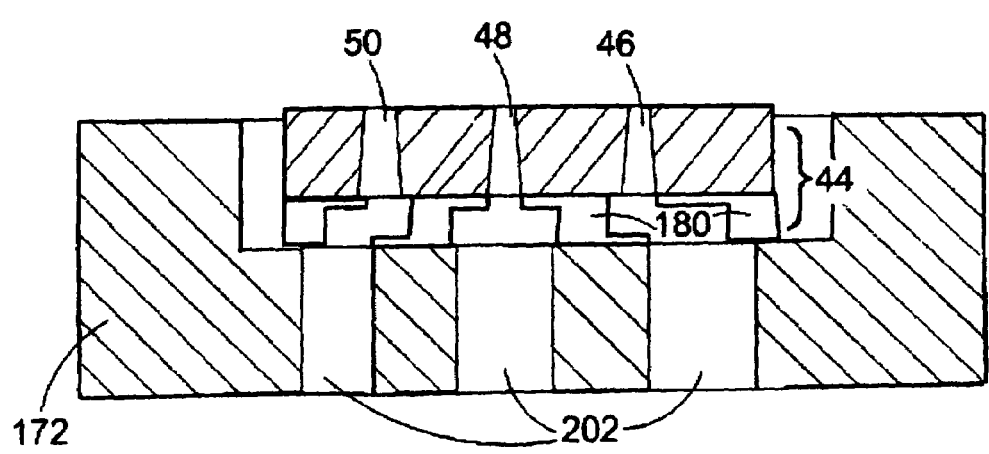

In another embodiment, illustrated in FIG. 18, the manifold is provided by a multi-layer photoresist material 180. The multi-layer photoresist material 180 provides a greater degree of freedom in ejection head structure 44 design and body 172 design. FIGS. 19-23 illustrate one multi-layer photoresist material design which can enhance the adhesion of the head structure 44 to the body 172 without substantially blocking fluid flow paths 46-50 in the head structure 44.

Figure 19:
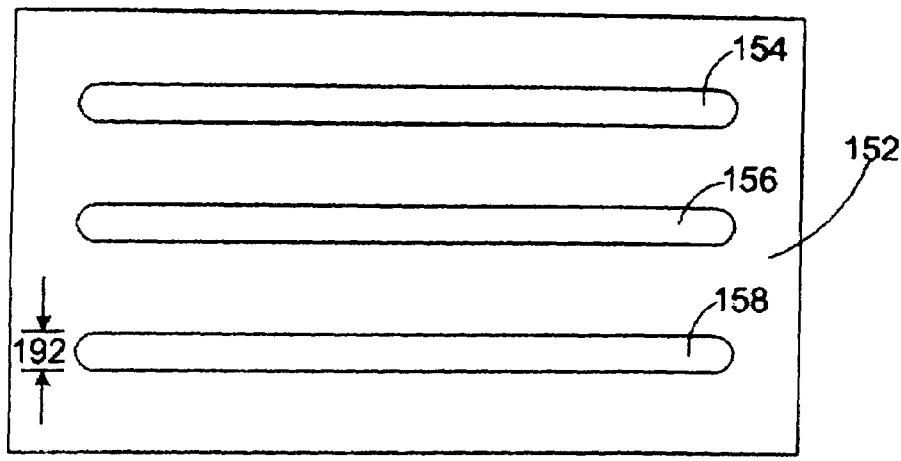
FIG. 19 is a plan view, not to scale, of an ejection head substrate according to one embodiment of the disclosure.
Figure 20:
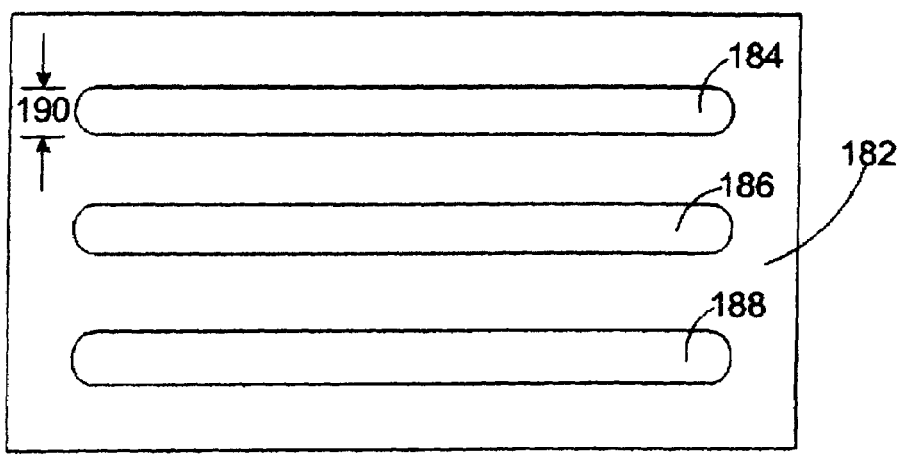
FIGS. 20-22 are plan views, not to scale, of photoresist material layers having flow channel portions patterned and developed therein according to an embodiment of the disclosure.
Figure 21:
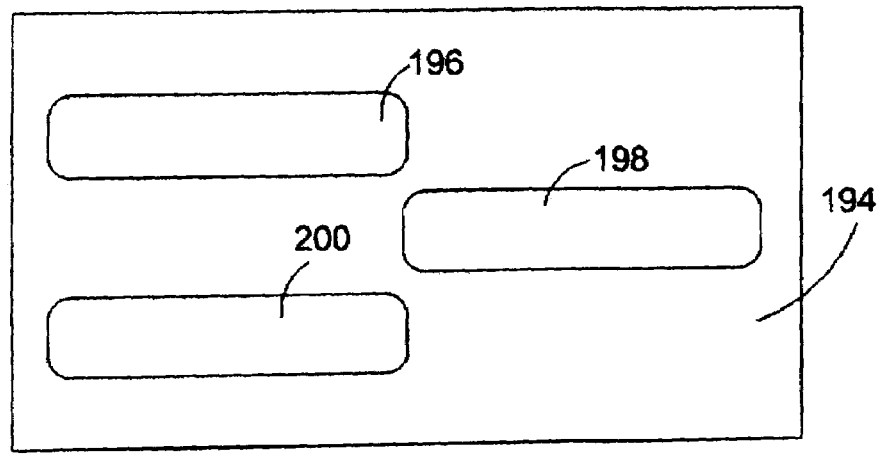
Figure 22:
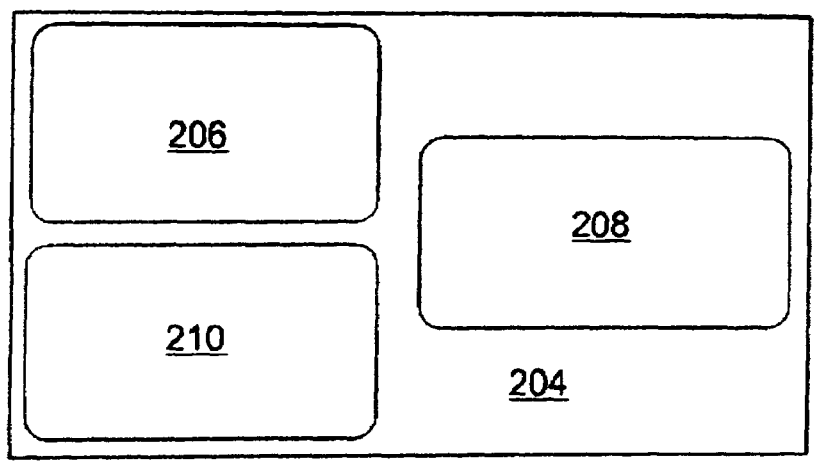

FIG. 19 is a plan view of a fluid supply side of a head substrate 152 having fluid supply paths 154-158. A first layer of photoresist material 182 contains fluid flow channels portions 184, 186 and 188 which have a larger open area than the fluid flow paths 154-158. Accordingly, each of the fluid flow channels portions 184, 186, and 188 have a width dimension 190 that is from about 1 to about 200% wider than the fluid flow path width 192 of the ejection head structure 44. The width dimension 190 improves fluidic flow to the fluid flow paths 154-158 while providing sufficient area for reliably sealing between the fluid flow paths 154-158.

Figure 23:
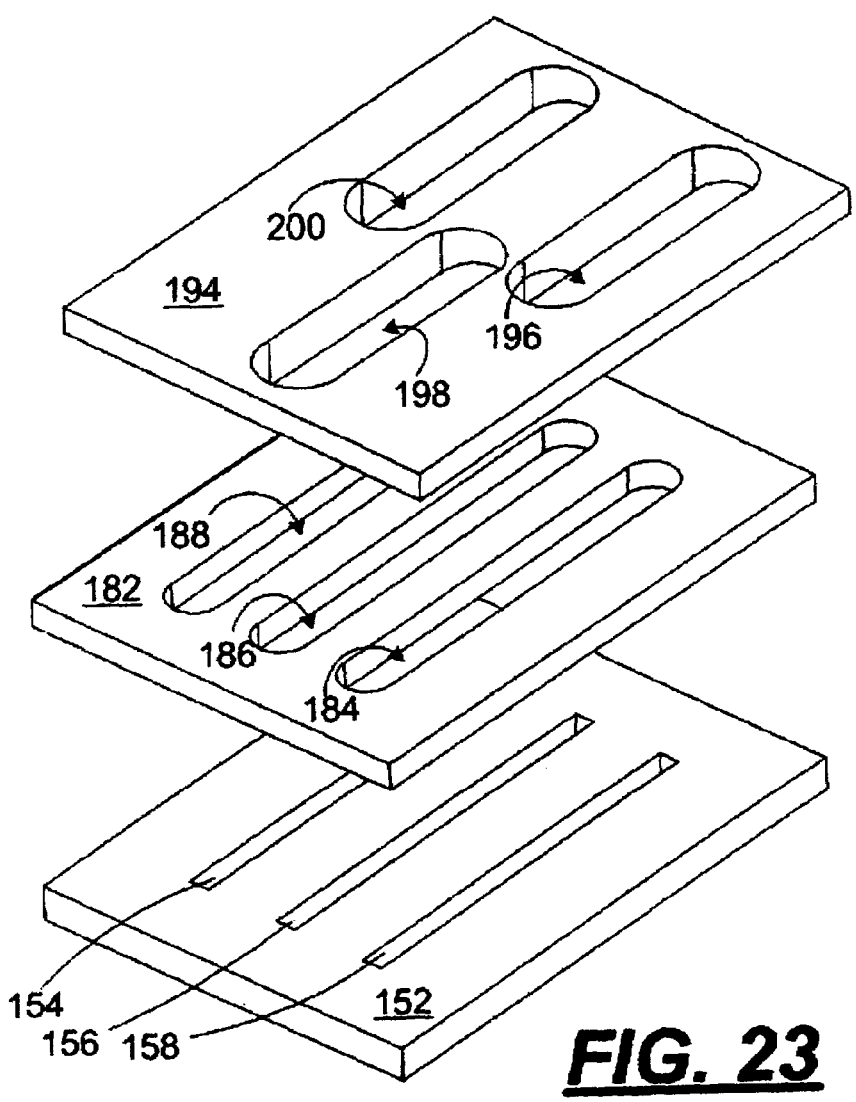
FIG. 23 is an exploded view, not to scale, of an ejection head substrate and two photoresist material layers according to an embodiment of the disclosure.

In a next photoresist layer 194, fluid flow channel portions 196, 198, and 200 have flow areas substantially the same as the flow areas of channel portions 184, 186, and 188, however the flow channel portions 196, 198, and 200 are substantially shorter than the flow channel portions 184, 186 and 188. The shorter flow channel portions 196, 198, and 200 provide increased surface area adjacent the flow channel portions 196, 198 and 200 for sealing fluid supply paths 202 in the body 172 (FIG. 18). However, the flow channel portions 196, 198, and 200 are sufficient to direct the fluid to the intended fluid flow paths 154-158. Additional photoresist layers can be provided, such as layer 204 containing fluid flow channel portions 206, 208, and 210 therein for flow communication with fluid flow paths 154-158. For illustrative purposes only, FIG. 23 illustrates an overlay of the photoresist layer 194 on the photoresist layer 182 which is laminated to the ejection head substrate 152.

Each of the photoresist layers 182, 194, and 204 would be applied, as by a photoresist laminate, spin coating, spraying, or screening to the fluid supply side 160 of the wafer 150. The photoresist layers 182, 194, and 204 may be applied before or after forming the fluid flow paths 46-50 in the substrate 152. After applying the photoresist layers 182, 194, and 204 to the wafer 150, each of the photoresist layers 182, 194, and 204 may be patterned and developed as describe above with reference to FIGS. 11-16.

Certain photoresist layers 182, 194, and 204 may be selected from materials that enable direct attachment of the ejection head structure 44 to the body 172 using, for example, a thermal compression bonding process wherein heat and pressure are applied to the ejection head structure 44. Heat may be used to initially laminate a photoresist layer or layers to the wafer 150. A secondary heating process may then be used to adhere the photoresist layer or layers to the body 172.

For example, a negative photoresist material may be laminated or applied to the fluid supply side 160 of the wafer 150 using a dry film photoresist containing thermoplastic component such as the material described in U.S. Pat. No. 5,907,333 or a B-staged photoresist such as HD4000 polyimide photoimagable resist. After the photoresist layer is developed, a secondary heating process may allow the photoresist layer to be adhered directly to the body 172.

An alternate process may include a negative photoresist material that is laminated or applied to the fluid supply side 160 of the wafer 150 prior to forming the fluid flow paths 154-158 in the substrates 152. The negative photoresist material could be patterned but not developed and would thus act as an etch stop for forming the fluid flow paths 154-158 in the substrates 152 (e.g., where the fluid flow paths are formed using a process such as deep reactive ion etching). After forming the fluid flow paths, 154-158, the negative photoresist material may be developed to provide the desired flow channel features. The photoresist material may then either be bonded directly or with an adhesive to body 172.

An alternative process may include waiting until the fluid flow paths are formed in the substrates and the nozzle plates are attached to the substrates before laminating a photoresist material to the fluid supply side 160 of the wafer 150. In this process, a curable or thermoset photoresist material may be used to attach the ejection head structure 44 to the body 172. In the case of a thermoset photoresist material, the photoresist material may be cured when in contact with the body 172, or may be cured before attaching the ejection head structure 44 to the body 172. The cured photoresist material may also be attached to the body 172 by use of an adhesive as described above.

As will be appreciated, the foregoing embodiments enable production of micro-fluid ejection device structures having a supply path density ranging from greater than $1.00 \text{ mm}^{-1}$ up to about $3.0 \text{ mm}^{-1}$. The increased supply path density enables the use of smaller substrates thereby reducing the cost of the micro-fluid ejection device structures.

It is contemplated, and will be apparent to those skilled in the art from the preceding description and the accompanying drawings, that modifications and changes may be made in the embodiments of the invention. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. A method of making a multi-fluid cartridge for holding multiple fluids in segregated containment localities, a cartridge body containing fluid supply paths in fluid flow communication with the containment localities, the method comprising:

printing an adhesive with a bond line density of at least about $1.2 \text{ mm}^{-1}$ on a fluid supply side of a micro-fluid ejection device structure; and adhesively bonding a circuit device, attached to the micro-fluid ejection device structure, to the cartridge body for flow of fluid from containment localities to a device side of the micro-fluid ejection device structure, wherein the act of printing comprises one of stencil printing and screen printing, and wherein the micro-fluid ejection device structure is one of a plurality of micro-fluid ejection device structures diced from a wafer, each of the micro-fluid ejection device structures comprises an ejection head substrate and a nozzle plate, further comprising:

applying a photoresist layer to the wafer adjacent a fluid supply side of the ejection head substrates; and photodefining fluid flow channels in the photoresist layer to provide fluid flow channels therein in fluid flow communication with fluid flow paths in the ejection head substrates.

2. The method of claim 1 wherein applying the photoresist layer to the wafer comprises one of spin coating and spray coating a photoresist layer on the wafer.

3. The method of claim 1 wherein applying the photoresist layer to the wafer comprises spray coating a photoresist layer on the wafer.

4. The method of claim 1 wherein applying the photoresist layer to the wafer comprises web laminating the photoresist layer to the wafer.

5. The method of claim 1 wherein applying the photoresist layer to the wafer comprises laminating two or more photoresist layers to the wafer, each of the layers having photodefined fluid channels formed therein.

6. The method of claim 1, further comprising:

attaching the nozzle plate to a device side of each of the ejection head substrates on the wafer, each of the ejection head substrates having a fluid supply side and two or more of the fluid flow paths therein for supplying fluid from the supply side to the device side of the election head substrates, wherein the fluid flow paths in the ejection head substrates have a flow path density of greater than about 1.0 flow paths per millimeter.

7. The method of claim 6 further comprising photodefining the fluid flow channels in the photoresist layer prior to attaching the nozzle plat to the substrates.

8. The method of claim 6, further comprising attaching the circuit device to the device side of each of the ejection head substrates.

9. The method of claim 8, wherein the circuit device is attached to the device side of each of the substrates prior to stencil printing the adhesive.

10. The method of claim 1, wherein the adhesive is stencil printed after the wafer is diced.

11. A method of making a multi-fluid cartridge for holding multiple fluids in segregated containment localities, a cartridge body containing fluid supply paths in fluid flow communication with the containment localities, the method comprising:

printing an adhesive with a bond line density of at least about 1.2 mm$^{-1}$ on a fluid supply side of a micro-fluid ejection device structure; and adhesively bonding the micro-fluid ejection device structure to the cartridge body for flow of fluid from containment localities to a device side of the micro-fluid ejection device structure wherein the act of printing comprises one of stencil printing and screen printing, and wherein the micro-fluid ejection device structure is one of a plurality of micro-fluid ejection device structures diced from a wafer, each of the micro-fluid ejection device structures comprises an ejection head substrate and a nozzle plate, further comprising:

applying a photoresist layer to the wafer adjacent a fluid supply side of the ejection head substrates; and photodefining fluid flow channels in the photoresist layer to provide fluid channels therein in fluid flow communication with fluid flow paths in the ejection head substrates.

12. A method of making a multi-fluid cartridge for holding multiple fluids in segregated containment localities a cartridge body containing fluid supply paths in fluid flow communication with the containment localities, the method comprising:

printing an adhesive with a bond line density of at least about 1.2 mm$^{-1}$ on a cartridge body; and adhesively bonding a micro-fluid ejection device structure to the cartridge body for flow of fluid from containment localities to a device side of the micro-fluid ejection device structure, wherein the act of printing comprises one of stencil printing and screen printing, and wherein the micro-fluid ejection device structure is one of a plurality of micro-fluid ejection device structures diced from a wafer, each of the micro-fluid ejection device structures comprises an ejection head substrate and a nozzle plate, further comprising:

applying a photoresist layer to the wafer adjacent a fluid supply side of the ejection head substrates; and photodefining fluid flow channels in the photoresist layer to provide fluid channels therein in fluid flow communication with fluid flow paths in the ejection head substrates.

13. A method of making a multi-fluid cartridge for holding multiple fluids in segregated containment localities, a cartridge body containing fluid supply paths in fluid flow communication with the containment localities, the method comprising:

printing an adhesive with a bond line density of at least about 1.2 mm$^{-1}$ on a cartridge body; and adhesively bonding a circuit device attached to a micro-fluid ejection device structure to the cartridge body for flow of fluid from containment localities to a device side of the micro-fluid ejection device structure, wherein the act of printing comprises one of stencil printing and screen printing and wherein the micro-fluid ejection device structure is one of a plurality of micro-fluid ejection device structures diced from a wafer each of the micro-fluid ejection device structures comprises an ejection head substrate and a nozzle plat further comprising:

applying a photoresist layer to the wafer adjacent a fluid supply side of the ejection head substrates; and photodefining fluid flow channels in the photoresist layer to provide fluid channels therein in fluid flow communication with fluid flow paths in the ejection head substrates.

* * * * *